United States Patent [19]

Kimura et al.

[11] 4,122,089

[45] Oct. 24, 1978

[54] AMINOTHIOFLUORAN COMPOUNDS, PROCESS FOR THE PRODUCTION THEREOF, AND RECORDING ELEMENTS CONTAINING THE SAME

[75] Inventors: Shiro Kimura, Odawara; Yasuyoshi Nakamura, Hiratsuka; Shigeki Kurimoto, Hiratsuka; Katuhiro Motouchi, Hiratsuka, all of Japan

[73] Assignee: Sankio Chemical Co., Ltd., Tokyo, Japan

[21] Appl. No.: 771,857

[22] Filed: Feb. 23, 1977

[30] Foreign Application Priority Data

Feb. 23, 1976 [JP] Japan .................. 51-18003
Feb. 23, 1976 [JP] Japan .................. 51-18004
Feb. 23, 1976 [JP] Japan .................. 51-18005
Dec. 24, 1976 [JP] Japan .................. 51-155124

[51] Int. Cl.² .......................................... C07D 497/10
[52] U.S. Cl. ................................... 260/328; 544/145; 260/293.57; 260/326.5 SA; 260/454; 260/576; 260/578; 428/326; 428/537; 428/913
[58] Field of Search ............... 260/328, 335, 325 PH, 260/293.57, 326.5 SA; 544/145

[56] References Cited

U.S. PATENT DOCUMENTS

| | | | |
|---|---|---|---|
| 3,185,696 | 5/1965 | Tien .................. | 260/295 |
| 3,654,314 | 4/1972 | Farber et al. .......... | 260/343.3 |
| 3,837,889 | 9/1974 | Hughes et al. ......... | 117/36.2 |
| 3,864,145 | 2/1975 | Seki et al. ........... | 117/36.2 |
| 3,876,659 | 4/1975 | Houlihan et al. ...... | 260/326.1 |

OTHER PUBLICATIONS

Meyer et al, Ber. Deut. Chem., vol. 33, pp. 2577 to 2584 (1900).
Beilstein's Handbuch der Organischen Chemie, 4th Ed. vol. 19, Main Werke, system No. 2835, pp. 234–235, Verlag Von Julius Springer, Berlin, Germany (1934).

*Primary Examiner*—John D. Randolph
*Attorney, Agent, or Firm*—Sughrue, Rothwell, Mion, Zinn and Macpeak

[57] ABSTRACT

A compound capable of forming a color on contact with an electron accepting compound and useful as a chromogenic material for recording members represented by the general formula (I)

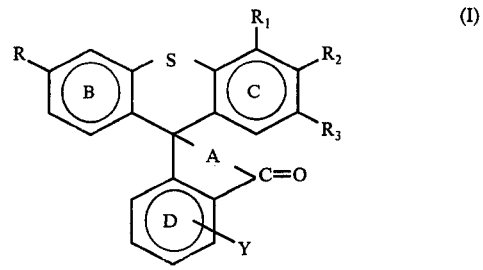

wherein A represents an oxygen atom or a group capable of forming a lactam ring with benzen ring D; Y represents a hydrogen atom or a functional group (such as a halogen atom or a nitro group); and when A is an oxygen atom, R represents an amino, i.e., unsubstituted, group or a substituted amino group; $R_1$ and $R_3$, which may be the same or different, each represents a hydrogen atom, a lower alkyl group, a nitro group, an amino group, or a substituted amino group; and $R_2$ represents a hydrogen atom or a lower alkyl group; wherein $R_1$ and $R_2$ or $R_2$ and $R_3$ may combine with benzene ring C to form a nitrogen-containing heterocyclic ring condensed therewith; and when A is a group capable of forming a lactam ring with benzene ring D, R represents

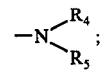

$R_2$ represents

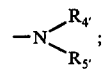

$R_4'$, $R_4$, $R_5$ and $R_5'$, which may be the same or different, each represents a hydrogen atom or a lower alkyl group; and $R_1$ and $R_3$ each represents a hydrogen atom; processes for the production thereof; and recording members containing the same.

19 Claims, No Drawings

AMINOTHIOFLUORAN COMPOUNDS, PROCESS FOR THE PRODUCTION THEREOF, AND RECORDING ELEMENTS CONTAINING THE SAME

BACKGROUND OF THE INVENTION

1. Field of the Invention

The present invention relates to novel aminothiofluoran compounds and novel aminothiofluoran-γ-lactam compounds. The invention further relates to processes of producing these compounds and recording members and elements containing these compounds as dye-forming materials or chromogenic materials e.g., color forming materials.

2. Description of Prior Art

Recording methods in which a color is formed, for example, pressure-sensitive copying materials, heat-sensitive recording materials, etc., employing colorless electron donating chromogenic materials (sometimes designated color forming materials or color formers) are already widely known and used commercially, and various colorless chromogenic compounds are known. In particular, fluoran compounds as examples of these colorless chromogenic compounds have preferred properties in that when they are brought into contact with an electron accepting developer (sometimes designated color developing materials or color developers) such as active clay, a phenol resin, etc., an immediate coloration occurs resulting in colors having a very wide range of various color tones and the colors or dyes thus formed have superior light resistance, water resistance, and color density. As a result of these desirable characteristics fluoran compounds have been actively investigated in this art and recording technique systems using these fluoran compounds have been greatly developed at present.

Processes for producing fluoran compounds in which the oxygen atom at the 10-position of the fluoran nucleus is replaced by a sulfur atom, that is, thiofluoran compounds represented by the general formula (VI)

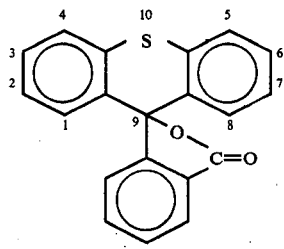

(VI)

are reported in R. Meyer and J. Szaneck Ber., 33, 2577(1900) and Wyler *Dissertation* (Zürich 1894) but these investigators only reported that symmetric 3,6-substituted aminothiofluoran compound could be obtained by reacting fluorescein and sodium sulfide under alkaline conditions to form thiofluorescein, halogenating the thiofluorescein, and then aminating the product but no reports on asymmetric aminothiofluoran compounds are known. In this connection, the aminothiofluoran compounds of this invention represented by general formula (I) as will be shown below cannot be produced by the process reported by R. Meyer et al.

SUMMARY OF THE INVENTION

As the result of various investigations, novel asymmetric aminothiofluoran compounds represented by the following general formula (I) have now been developed and it has now also been found that these asymmetric aminothiofluoran compounds can be used as excellent chromogenic materials for recording members forming a color.

Accordingly, this invention provides a compound capable of forming a color on contact with an electron accepting compound and useful as a chromogenic material for recording members represented by the general formula (I)

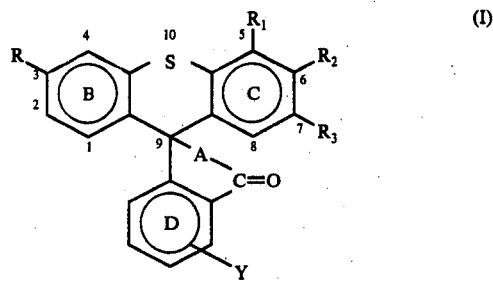

(I)

wherein A represents an oxygen atom or a group capable of forming a lactam ring with benzene ring D; Y represents a hydrogen atom or a functional group (such as a halogen atom or a nitro group); and when A is an oxygen atom, R represents an amino group or a substituted amino group; $R_1$ and $R_3$, which may be the same or different, each represents a hydrogen atom, a lower alkyl group, a nitro group, an amino group, or a substituted amino group; and $R_2$ represents a hydrogen atom or a lower alkyl group; wherein $R_1$ and $R_2$ or $R_2$ and $R_3$ may combine with benzene ring C to form a nitrogen-containing heterocyclic ring condensed therewith, and when A is a group capable of forming a lactam ring with benzene ring D, R represents

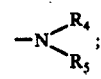

$R_2$ represents

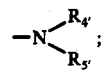

$R_4$, $R_{4'}$, $R_5$ and $R_{5'}$, which may be the same or different, each represents a hydrogen atom or a lower alkyl group; and $R_1$ and $R_3$ each represents a hydrogen atom.

Further, according to one embodiment of this invention, there is provided a novel aminothiofluoran compound represented by the general formula (Ia)

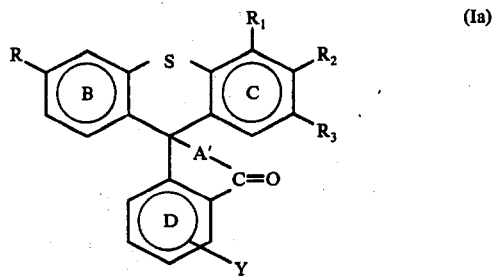

(Ia)

wherein A' represents an oxygen atom; R represents an amino group or a substituted amino group; $R_1$ and $R_3$, which may be the same or different, each represents a hydrogen atom, a lower alkyl group, a nitro group, an amino group or a substituted amino group; $R_2$ represents a hydrogen atom or a lower alkyl group; $R_1$ and $R_2$ or $R_2$ and $R_3$ may combine with benzene ring C to form a nitrogen-containing heterocyclic ring; and Y represents a hydrogen atom or a functional group.

According to another embodiment of this invention, there is provided a novel aminothiofluoran-γ-lactam compound represented by general formula (Ib)

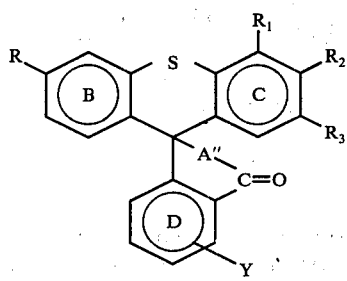

(Ib)

wherein A" represents a group capable of forming a lactam ring with benzene ring D; R represents

$R_2$ represents

$R_4$, $R_{4'}$, $R_5$ and $R_{5'}$ which may be the same or different, each represents a hydrogen atom or a lower alkyl group; $R_1$ and $R_3$ each represents a hydrogen atom; and Y represents a hydrogen atom or a functional group.

In an even further embodiment of this invention, the invention provides a process for producing the aminothiofluoran compound of this invention represented by general formula (I) (wherein A is an oxygen atom) i.e. represented by the general formula (Ia)

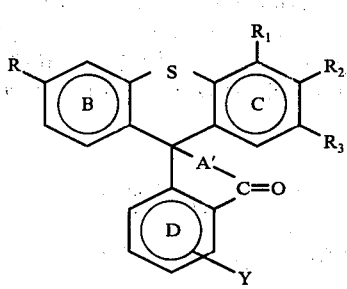

(Ia)

wherein A' is an oxygen atom and wherein R, $R_1$, $R_2$, $R_3$ and Y are as defined above; which comprises reacting a diphenyl sulfide derivative represented by general formula (II)

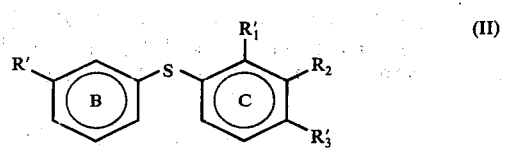

(II)

wherein R' represents a substituted amino group; $R_{1'}$ and $R_{3'}$, which may be the same or different, each represents a hydrogen atom, a lower alkyl group, a nitro group, an amino group or a substituted amino group; and $R_2$ represents a hydrogen atom or a lower alkyl group; $R_{1'}$ and $R_2$ or $R_2$ and $R_{3'}$ may combine with benzene ring C to form a nitrogen-containing heterocyclic ring; with phthalic anhydride or a nucleus substituted derivative thereof.

In additional embodiment of this invention, the invention provides a process for producing the aminothiofluoran compound of this invention represented by the general formula (I) (wherein A is an oxygen atom), i.e., represented by the general formula (Ia)

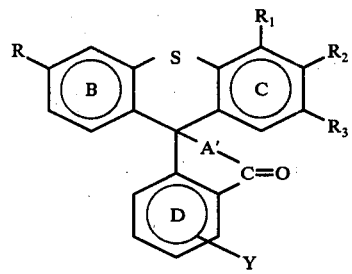

(Ia)

wherein R, $R_1$, $R_2$, $R_3$, A' and Y are as described above; which comprises reacting a benzoylbenzoic acid derivative represented by general formula (III)

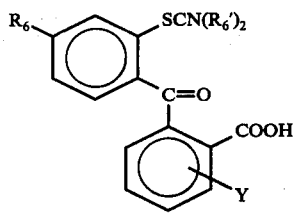

(III)

wherein $R_6$ represents a substituted amino group; $R_6'$ represents a lower alkyl group; and Y is as described above; with a phenol derivative represented by general formula (IV)

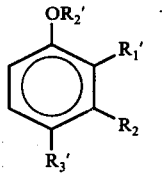

(IV)

wherein $R_2$ and $R_2'$, which may be the same or different, each represents a hydrogen atom or a lower alkyl group; and $R_1'$ and $R_3$, which may be the same or different, each represents a hydrogen atom, a lower alkyl group, a nitro group, an amino group or a substituted amino group; $R_1'$ and $R_2$ or $R_2$ and $R_3'$ may combine with the benzene ring to form a nitrogen-containing heterocyclic ring.

In a still further embodiment of this invention, the invention provides a process for producing the aminothiofluoran-γ-lactam compound of this invention represented by general formula (I) (wherein A is a group capable of forming a lactam ring with benzene ring D) i.e., represented by the general formula (Ib)

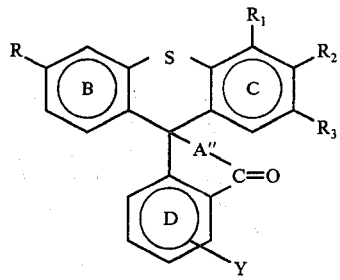
(Ib)

wherein A" is a group capable of forming a lactam ring with benzene ring D and R, $R_1$, $R_2$, $R_3$, and Y are as described above; which comprises reacting an aminothiofluoran compound represented by general formula (V)

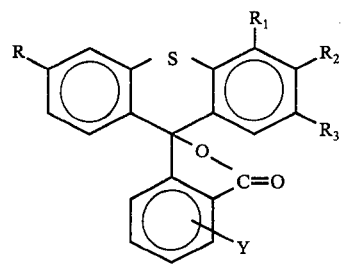
(V)

wherein R represents

$R_2$ represents

$R_4$, $R_4'$, $R_5$ and $R_5'$, which may be the same or different, each represents a hydrogen atom or a lower alkyl group; $R_1$ and $R_3$ each represents a hydrogen atom; and Y is as described above; or an acid addition salt thereof; with ammonia, a primary amine or a hydrazine derivative.

The present invention also provides in an additional embodiment a recording element comprising a support having therein or thereon a recording material containing at least one aminothiofluoran compound or at least one aminothiofluoran-γ-lactam compound represented by general formula (I) as a chromogenic material.

DETAILED DESCRIPTION OF THE INVENTION

The asymmetric aminofluoran compounds of this invention, for example, the aminothiofluoran compounds represented by the general formula (Ia)

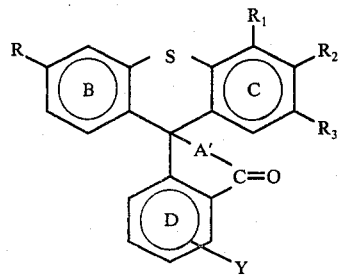
(Ia)

wherein the compound has the same or different amino groups or substituted amino groups at the 3-position, or the 3- and 5-positions, or the 3-, 7-positions, or 3-, 5-, 7-positions, etc., are stable in the air, and the compounds are powders which are substantially colorless or have a light color, are soluble in various volatile solvents (e.g., chloroform, toluene, etc.) or nonvolatile organic solvents (e.g., monoisopropyldiphenyl, diisopropylnaphthalene, etc.) The asymmetric aminofluoran compound can quickly and clearly form colors of various color tones when they are brought into contact with or melted together with an electron accepting material, i.e., an acid, e.g., as a sollid, as a gas, or in a solution, such as acid clay, bentonite, benzoic acid, naphthol, a phenol-formaldehyde resin, a hydrolyzed maleic anhydride-styrene copolymer, etc., or further when an organic solution of the compound or compounds is treated with an acid.

Moreover, it has been found that these compounds of this invention have excellent properties such as high coloration rate, color density, light resistance, water resistance, oilsolubility, and non-sublimation properties. In addition, it is possible to control the color tone using the aminothiofluoran compounds of this invention together with known chromogenic materials or by using a mixture of the compounds of this invention. These properties are preferred characteristics as chromogenic materials for pressure-sensitive copying papers, heat-sensitive recording papers, light-sensitive papers, coloring inks, etc. Thus, the aminothiofluoran compounds of this invention are very useful and, in particular, can be suitably used as chromogenic materials for pressure-sensitive copying papers and heat-sensitive recording papers.

As described above, in an embodiment of this invention the asymmetric aminothiofluoran compound of this invention represented by general formula (Ia) can be prepared by Process A through the diphenyl sulfide derivative represented by general formula (II) or by Process B through the benzoylbenzoic acid derivative represented by general formula (III) as set forth below.

Process A

The aminothiofluoran compound of this invention represented by general formula (Ia) can be prepared by reacting a diphenyl sulfide derivative represented by the general formula (II)

(II)

wherein R' represents a substituted amino group; R₁' and R₃', which may be the same or different, each represents a hydrogen atom, a nitro group, an amino group, or a substituted amino group; and R₂ represents a hydrogen atom or a lower alkyl group; R₁' and R₂ or R₂ and R₃' may combine with benzene ring C to form a nitrogen-containing heterocyclic ring and phthalic anhydride or a nucleus substituted derivative thereof in the presence of a condensing agent and, if desired, converting a part or all of the substituted amino groups R', R₁', and R₃' into an unsubstituted amino group or groups.

Process B

The aminothiofluoran compound of this invention represented by general formula (Ia) can also be prepared by reacting a benzoylbenzoic acid derivative (including the hydrate thereof) represented by the general formula (III)

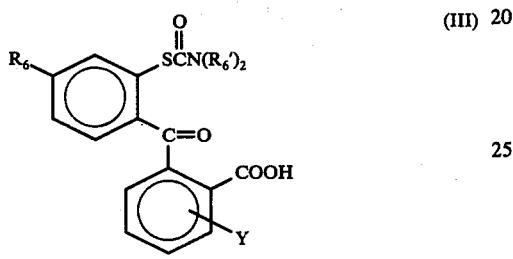

and a phenol derivative represented by the general formula (IV)

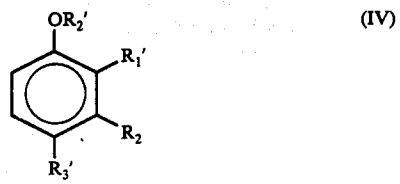

wherein R₂ and R₂', which may be the same or different, each represents a hydrogen atom or a lower alkyl group; R₁' and R₃', which may be the same or different, each represents a hydrogen atom, a lower alkyl group, a nitro group, an amino group, or a substituted amino group; R₁' and R₂ or R₂ and R₃' may combine with the benzene ring to form a naphthalene nucleus or a nitrogen-containing heterocyclic ring.

In addition, when at least one of R, R₁ and R₃ of the aminothiofluoran compound of this invention represented by general formula (Ia) is an amino group (i.e., an unsubstituted amino group), the amino group can be, if desired, converted into a substituted amino group by reacting with an appropriate reactant.

Process A comprises the reaction steps as shown more specifically in the following reaction schematic A:

Reaction Schematic A

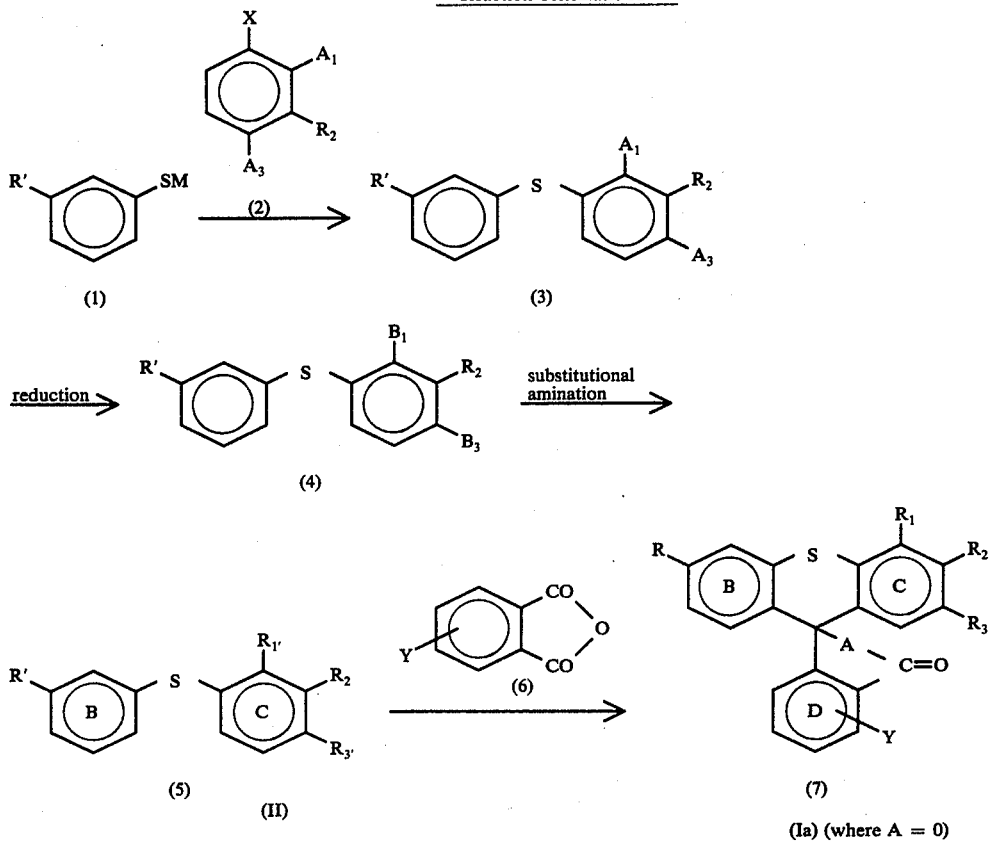

wherein R₆ represents a substituted amino group; R₆' represents a lower alkyl group e.g., having 1 to 6 carbon atoms; and Y represents a hydrogen atom or a functional group, such as a halogen atom and a nitro group, wherein, M represents a hydrogen atom or an alkali metal atom; X represents a halogen atom (e.g., chlorine, bromine, iodine, etc.); A₁ and A₃, which may be the same or different, each represents a hydrogen atom or a nitro group; $B_1$ and $B_3$ each represents a hydrogen atom or an amino group; and R; R'; $R_1'$ $R_1$; $R_2$; $R_3$; $R_3'$; A; and Y have the same significance as above.

That is, in the reaction schematic A, by condensing a m-substituted aminothiophenol derivative or an alkali metal salt thereof such as a sodium salt, potassium salt, etc., (1) and an unsubstituted or o- and/or p-mono or di-nitrohalobenzene derivative (2), the diphenyl sulfide derivative (3) is obtained. In this case, an alcoholic solvent (such as methanol, ethanol, isopropanol, etc.) is suitably used.

The aminosubstituted diphenyl sulfide derivative (4) is then obtained by chemically reducing the diphenyl sulfide derivative (3) with a metal, such as iron or zinc, in the presence of an acid, such as hydrochloric acid, acetic acid, etc., or by catalytically reducing the diphenyl sulfide derivative (3) under a hydrogen stream in the presence of a catalyst such as Raney nickel, palladium black, etc. In the latter case, the reduction can be easily performed at a hydrogen pressure of about 25 to about 50 kg/cm$^2$ and at a reaction temperature of about 40° to about 100° C.

Then, the reaction of obtaining the substituted aminodiphenyl sulfide derivative (5) from the aminosubstituted diphenyl sulfide derivative (4) thus formed can be achieved by reacting the amino-substituted diphenyl sulfide derivative (4) and an appropriate reactant in a known manner to introduce a necessary substituent into the amino group. Typical examples of appropriate reactants which can be used for this purpose, e.g., in an amount of about 1 to 10 moles per mole of the diphenyl sulfide derivative (4), are alkylating agents such as methyl chloride, ethyl iodide, isoamyl bromide, diethyl sulfate, monochloroacetic acid, ethylene chlorohydrin, benzyl chloride, bromocyclohexyl, acetaldehyde, benzaldehyde, and cyclohexanone (the latter three compounds are by the reduction of the Schiff base); acylating agents such as acetic anhydride, benzoic anhydride, benzoyl chloride; sulfonylating agents such as p-toluenesulfonyl chloride, methanesulfonyl chloride, pyridinecarboxylic acid chloride, pyridinesulfonyl chloride, 8-quinolinsulfonyl chloride; arylating agents such as iodobenzene, nitrochlorobenzene, o-bromobenzoic acid, 1-chloromethyl naphthalene, and 2-bromo-3-naphthic acid; urea; and the derivatives of these above-described reactants.

In the above-described reaction, when $A_1$ and $A_3$ of the diphenyl sulfide derivative (3) are not a nitro group, the subsequent reduction reaction and substitutional amination reaction are as a matter of course omitted. Furthermore, when the substituted aminodiphenyl sulfide derivative (5) is, in particular, the 3,4'-substituted aminodiphenyl sulfide derivative, the derivative is obtained by a process of reacting 3-nitrobenzenesulphenyl chloride and an N-substituted aniline derivatives as described in, for example, H. Z. Lecher; *J. Org. Chem.* 20, 475 (1955). In the above steps, temperatures at about reflux are used and a suitable reaction time generally ranges from about 2 to about 24 hours.

Preferred examples of the groups represented by R', $R_1'$, $R_2$ and $R_3'$ in the above-described substituted aminodiphenyl sulfide derivative (5) are a hydrogen atom, a halogen atom (e.g., chlorine, bromine, iodine, etc.), a lower alkyl group (e.g., methyl, ethyl, isopropyl, n-butyl, tert-butyl, sec-butyl, etc.), a lower alkoxy group (e.g., methoxy, ethoxy, isopropoxy, etc.), a nitro group, a hydroxy group, a carboxy group, an acyl group (e.g., formyl, acetyl, benyoyl, etc.), a carboxamido group (e.g., phenylacetamido, toluoylamino, etc.), a sulfonamido group (e.g., N-benzyl-N-phenylsulfonamido, toluenesulfonamido, phenylsulfonamido, etc.), an aryl group (e.g., phenyl, naphthyl, tolyl, etc. which can be substituted with any substituents for example, methyl, nitro, carboxy, etc.), a benzyl group, a benzyloxy group an aliphatic amine residue, an alicyclic amine residue, a heterocyclic amine residue, an aromatic amine residue, etc., and as the case may be, $R_1'$ and $R_2$ or $R_2$ and $R_3'$ may combine with benzene ring C to form a naphthalene nucleus by the group of —CH═CH—CH═CH— or to form a nitrogen-containing heterocyclic ring, e.g., indole, carbazole, etc. In addition, the term "lower" as used herein means a bonding chain having 1 to 6 carbon atoms.

Suitable examples of exemplary but non-limitting aliphatic, aromatic, alicyclic and heterocyclic amine residues as described above include, e.g., methylamino, ethylamino, dimethylamino, diethylamino, N-acetyl-N-ethylamino, naphthalenemethyl amino, N-ethyl-N-benzylamino, N-benzylamino, anilino, N-ethylanilino, N-acetylanilino, N,N-diphenylamino, N-methyltoluidino, carboxyanilino, carboxy naphthylamino, phenylanilino, N-benzylanilino, pyrrolidino, piperidino, morpholino, cyclohexylamino, N-ethyl-N-cyclohexylamino, and derivatives thereof.

The aminothiofluoran compound (7) which is the desired compound of this invention represented by the general formula (Ia) can also be obtained by condensing the substituted aminodiphenyl sulfide derivative (5) and phthalic anhydride or the nucleus substitued derivative thereof (6) (e.g., phthalic anhydride, 4-nitrophthalic anhydride (where Y is a nitro group), 4-chlorophthalic anhydride (where Y is a chlorine atom) etc;) e.g., in a molar ratio of the substituted aminodiphenyl sulfide derivative (5) to the phthalic anhydride or nucleus substituted derivative thereof (6) of about 1:1 to 1:6 in the absence of a catalyst or in the presence of a Friedel-Crafts catalyst such as aluminum chloride, stannic chloride, zinc chloride, boron trifluoride, etc., in the absence of a solvent (e.g., by melting the reactants) or in the presence of an appropriate solvent such as carbon disulfide, tetrachloroethane, nitrobenzene, chlorobenzene, etc. (e.g., at temperatures up to about reflux), but the desired compound is preferably obtained by melting and reacting both of the above-described compounds in the presence of the above-described catalyst in the absence of a solvent and then adding thereto a condensing agent e.g., in an amount of about 3 to 30 times on a molar basis thereof. A suitable reaction time can range from about 1 to about 75 hours. Examples of suitable nucleus substituent groups for the phthalic anhydride, include functional groups such as, for example, a halogen atom and a nitro group. Examples of suitable condensing agents which can be used in the above condensation reaction are sulfuric acid, fuming sulfuric acid, phosphoric anhydride, polyphosphoric acid, anhydrous zinc chloride, phosphorus pentoxide, phosphorus oxychloride, etc., and these condensing agents may be used individually or as a mixture thereof. When, for example, 98% sulfuric acid is used as the condensing agent, the condensation reaction is carried out for about 1 to 40 hours at about 10° to 150° C., and the reaction can be completed within about 2 to 3 hours when the reaction is conducted at about 130° to about 150° C.

After the reaction is completed, the cooled reaction mixture is poured onto a large amount of crushed ice, an aqueous solution of an alkali such as sodium hydroxide is added to the reaction mixture to render the product mixture wealky alkaline, the reaction product thus precipitated is recovered by filtration, e.g., under suction, or extracted with benzene, chloroform, etc., and the solvent is distilled away. Then, the residue is purified by recrystallization to provide the colorless or lightly colored aminothiofluoran compound of this invention.

On the other hand, Process B comprises the reaction steps as shown in the following reaction schematic B:

Reaction Schematic B:

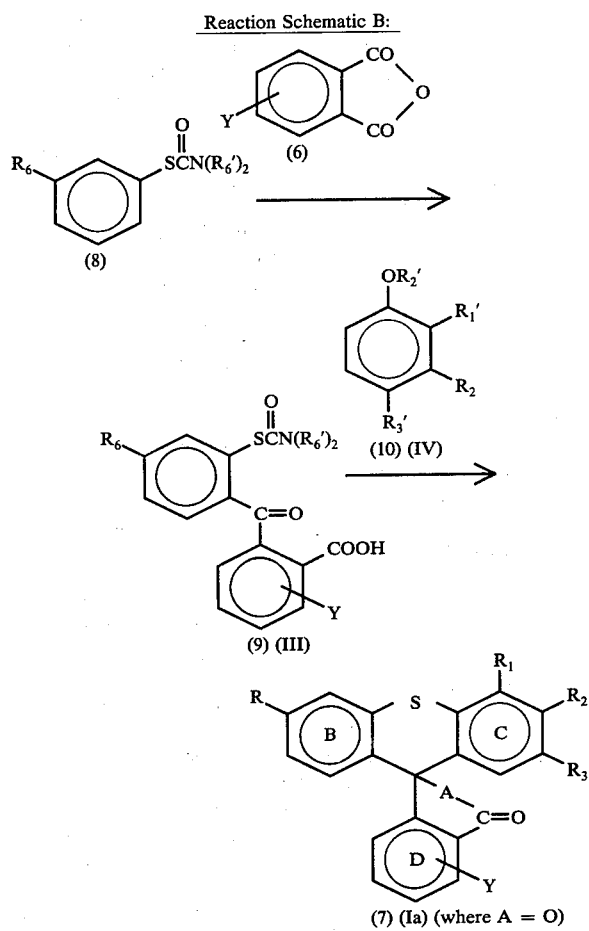

(7) (Ia) (where A = O)

wherein R; $R_1$; $R_2$; $R_3$; $R_1'$; $R_2'$; $R_3'$; $R_6$; $R_6'$; A; and Y have the same significance as above.

That is, in the reaction schematic B, the benzoylbenzoic acid derivative (including the hydrate thereof) (9) may be obtained by condensing the S-3-substituted aminophenyldialkylthiocarbamate (8) (see, for example, M. S. Newman et al.; *J. Org. Chem.*, 31, 3980 (1966) and phthalic anhydride or the nucleus substituted derivative thereof (6) using the condensation process as described in Process A, that is, in the absence of a catalyst or in the presence of a Friedel-Crafts catalyst such as aluminum chloride, stannic chloride, zinc chloride, boron trifluoride, etc., in the absence of a solvent or in the presence of a solvent such as carbon disulfide, tetrachloroethane, nitrobenzene, chlorobenzene, etc. but in this case also, it is preferred to melt and react both of the above described compounds in the presence of aluminum chloride as the catalyst in the absence of a solvent. After the reaction is completed, the reaction mixture is decomposed with hydrochloric acid followed by extraction, the extract is rendered weakly alkaline with sodium carbonate, and the precipitate formed is removed by filtration. The filtrate is acidified e.g., to a pH of about 4 to 6, and the precipitate thus formed is recovered by filtration to provide the benzoylbenzoic acid derivative (inlcuding the hydrate thereof) (9).

Furthermore, the aminothiofluoran compound (7) of this invention represented by general formula (Ia) can be obtained by reacting the compound (9) obtained in the above step and a phenol derivative (10) in the presence of a condensing agent. Examples of suitable condensing agents include sulfuric acid, fuming sulfuric acid, phosphoric anhydride, polyphosphoric acid, acetic anhydride, anhydrous zinc chloride, phosphorus pentoxide, phosphorus oxychloride, etc., can be used individually or as a mixture thereof.

When 98% sulfuric acid is used as the condensing agent, the condensation reaction is carried out under stirring for about 1 to about 50 hours at about 10° to about 150° C. Then, by following the same procedure as described above in the case of obtaining the aminothiofluoran compound (7) in the above described Process A, the desired product is obtained. Also, preferred groups represented by $R_1'$, $R_2$ and $R_3'$ in the phenol derivative (10) are the groups as illustrated in regard to compound (5) in Process A described above.

Also, if desired, the substituted aminothiofluoran compound (7) can be obtained by a condensation reaction of an aminothiofluoran compound having an amino group obtained in the above-described two processes, that is, the compound (7) wherein one or more groups of R, $R_1$ and $R_3$ are amino groups and the above-described appropriate reactant. Moreover, the aminothiofluoran compound represented by the general formula (Ia) wherein $R_1$, $R_3$ and/or Y are nitro groups or wherein $R_1$ and $R_2$ or $R_2$ and $R_3$ are combined with benzene ring C to form a carbazole group can also be obtained by a similar reaction, and the formation of the compound has been confirmed by thin layer chromatography for instance, a condensation product of 2(4'-dimethylamino-2'-dimethylaminocarbonylthiobenzoyl)benzoic acid and 1,2,3,4-tetrahydro-6-ethoxycarbazole is colored a red dark in the presence of silica gel.

In another embodiment of this invention, an aminothiofluoran-γ-lactam compound represented by general formula (Ib) wherein A" represents a group capable of forming a lactam ring with benzene ring D; R represents

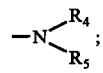

$R_2$ represents

wherein $R_4$, $R_4'$, $R_5$ and $R_5'$, which can be the same or different, each represents a hydrogen atom or a lower alkyl group; $R_1$ and $R_3$ each represents a hydrogen atom; and Y represents a hydrogen atom or a functional group can be prepared.

As colorless chromogenic materials which are colored red, fluoran series chromogenic compounds and fluoran-γ-lactam series chromogenic compounds are known at present. The latter type of fluoran compounds having a lactam ring, that is, rhodamine lactam compounds have been used practically for a long time as chromogenic materials and also appear in many publications. However, the aminothiofluoran-γ-lactam compounds of this invention represented by general formula (Ib) have never been reported in the art.

The aminothiofluoran compound of general formula (V) which is the starting material for producing the aminothiofluoran-γ-lactam compound of this invention represented by general formula (Ib) is unstable and is colored red as Rhodamine B derivatives and further is discolored with the passage of time when it is allowed to stand. On the other hand, it has been found that the aminothiofluoran-γ-lactam compounds of this invention represented by general formula (Ib) are stable in air, possess various desirable characteristics as chromogenic materials for pressure-sensitive copying papers, heat-sensitive recording papers, light-sensitive papers, etc., and hence are very useful compounds.

That is, in addition to the aminothiofluoran compounds of this invention represented by the general formula (Ia) described above, the aminothiofluoran-γ-lactam compounds of this invention represented by general formula (Ib) are colorless or lightly colored powders, soluble in various organic solvents, and form a red-purple color when they are brought into contact with an electron accepting material such as an inorganic solid acid, an organic acid, and a organic acid polymer as a powder or as a solution or when they are melted together with the electron accepting material. Furthermore, any desired color can be obtained by using the aminothiofluoran-γ-lactam compounds of this invention represented by the general formula (Ib) together with a known chromogenic material or materials.

Since the color hue formed by the aminothiofluoran-γ-lactam compounds of this invention represented by general formula (Ib) is shifted to a longer wave length side than those of the corresponding Rhodamine series chromogenic materials and aminofluoran-γ-lactam compounds, the compounds of this invention exhibit a purplish dark red color. Furthermore, the aminothiofluoran-γ-lactam compounds of this invention emit a strong fluorescence in a solution of a fatty acid such as formic acid, acetic acid, propionic acid, etc.

The aminothiofluoran-γ-lactam compound of this invention represented by general formula (Ib) can be prepared by reacting e.g., at reflux, an aminothiofluoran compound represented by the general formula (V)

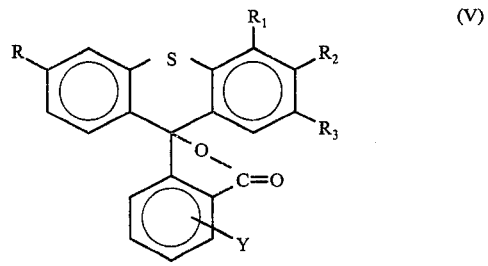
(V)

wherein R represents

$R_2$ represents

wherein $R_4$, $R_4'$, $R_5$ and $R_5'$, which may be the same or different, each represents a hydrogen atom or a lower alkyl group; $R_1$ and $R_3$ each represents a hydrogen atom; and Y represents a hydrogen atom or a functional group, such as a halogen atom (e.g., chlorine, bromine, iodine, etc.) and a nitro group or the acid addition salt thereof with more than an equivalent amount of ammonia, a primary amine or a hydrazine derivative, with examples of suitable acid addition salts of the above aminofluoran compound including the hydrochlorides, sulfates, perchlorates, etc. thereof, in an organic solvent or non-solvent, where in some cases phosphrous oxychloride can be effectively employed as a catalyst.

A suitable time for the reaction can range from about 2 to 10 hours. A suitable amount of the ammonia, primary amine and hydrazine derivative to the 3,6-bis-substituted aminothiofluoran derivative (V) can be a molar ratio of about 1:1 or higher when a solvent is used, about 3:1 to about 10:1 when no solvent is used.

Typical examples of primary amines or hydrazine derivatives which can be used in the above reaction are methylamine, ethylamine, propylamine, cyclohexylamine, aniline, toluidine, chloroaniline, nitroaniline, benzylaniline, naphthylamine, aminopyridine, aminoquinoline, methylhydrazine, ethylhydrazine, phenylhydrazine, tolylhydrazine, nitrophenylhydrazine, naphthylhydrazine, etc. Accordingly, depending on the kind of the amine or the hydrazine employed in the reaction, group A capable of forming the lactam bond in the compound of general formula (Ib) can be represented by $>N(NH)_nR_7$ wherein $R_7$ represents a hydrogen atom, an alkyl group, an alicyclic group, or an aromatic group and $n$ is 0 or 1 (e.g., $>NH(n=0)$, $>N-CH_3(n=0)$,

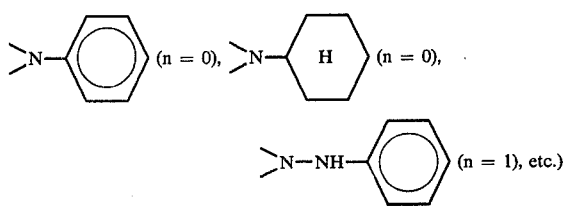

In addition, the 3,6-bis-substituted aminofluoran compound represented by general formula (V) may be prepared Process (C) or Process (D) shown below:

Process (C)

The compound (V) is prepared in accordance with the following reaction schematic

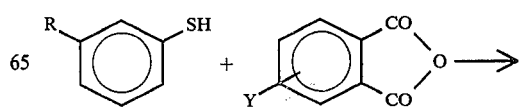
(11)     (6)

-continued

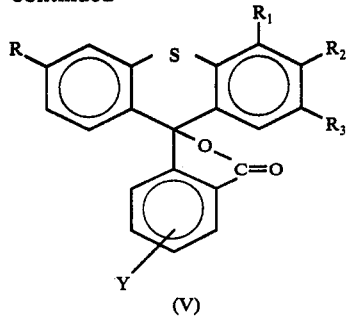

wherein in (V) when R$_2$ is R, R is

by refluxing or melting an m-substituted aminothiophenol derivative (11) and phthalic anhydride or a nucleus substituted derivative thereof (6) in an about 2:1 by molar ratio in the absence of a catalyst or in the presence of a Friedel-Crafts catalyst such as aluminum chloride, stannic chloride, etc., in the absence of a solvent or in the presence of an appropriate solvent such as carbon disulfide, tetrachloroethane, nitrobenzene, chlorobenzene, etc., but simply melting the above reactants in the presence of the above-described catalyst in the absence of a solvent is preferred. Functional groups such as a halogen atom and a nitro group can be used as the nucleus substituent of phthalic anhydride.

Process (D)

The compound can also prepared in accordance with the following reaction schematic

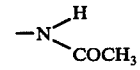

wherein in (V) when R$_2$ is R or R$_2$ is different from R, R is

and R$_2$ is $$N{\overset{R_4'}{\underset{R_5'}{\diagup}}}$$

by reacting a m-substituted aminothiophenol derivative (11) and a 2-(4'-substituted amino-2'-hydroxybenzoyl)-4 (or 5) - substituted benzoic acid (12) (e.g., where the substituent in the 4 (or 5) position is Y as defined above) in the presence of a condensing agent. For example, the reaction can be performed in the presence or absence of the above-described Friedel-Crafts catalyst using a condensing agent such as sulfuric acid, fuming sulfuric acid, polyphosphoric acid, phosphoric anhydride, acetic anhydride, acetic acid, phosphorus pentoxide, phosphorus oxychloride, etc. It is preferred for the reaction to be carried out e.g., for about 1 to 6 hours under heating in acetic anhydride as a solvent in the presence of the above-described catalyst, using a molar ratio of reactants of about 1:1.

Furthermore, the aminothiofluoran-γ-lactam compound of general formula (Ib) in which Y is a nitro group can be also obtained using a similar reaction and the formation of such a compound has been confirmed by thin layer chromatography.

In the above-descriptions, R', R$_1$', R$_2$', R$_3$', in general correspond to R, R$_1$, R$_2$, R$_3$, respectively, except as will be recognized by one skilled in the art modifications may occur therein due to the processing or reaction conditions employed or the kind of actual substituent involved e.g., where R', for example, is a substituted amino group, such may be converted into an unsubstituted amino group or vice versa, for example a $$-N{\overset{H}{\underset{COCH_3}{\diagup}}}$$

group may be converted to a $$-N{\overset{H}{\underset{H}{\diagup}}}$$

group.

Examples of the production of typical compounds of this invention are shown by the following Production Examples and embodiments of coloring record members using the compounds of this invention are also illustrated in detail by the following Examples but the invention should not be interpreted as being limited to these examples. Unless otherwise indicated herein, all parts, percents, ratios and the like are by weight.

Production Examples

Step (1) In 80 ml of methanol was dissolved 20.0 g of N,N-diethylamino-m-thiophenol (boiling point 103°–105° C./0.2 mm Hg) prepared according to the process of M. S. Newmann et al.; *J. Org. Chem.*, 31, 3980 (1966) and then 21.3 g of 28% by weight solution of sodium methoxide in methyl alcohol was added dropwise to the solution at a temperature below 15° C. Then, after adding gradually 19.2 g of p-nitro-chlorobenzene to the thus obtained solution, the resultant mixture was reacted for 5 hours at the refluxing temperature. The reaction mixture was cooled to room temperature (about 20° C.) and the crystals precipitated were recovered by filtration, washed with water, and crystallized from n-propanol to provide 29.4 g (yield 88%) of 3-diethylamino-4'-nitro-diphenyl sulfide. Melting point: 76.0°–76.5° C.

| Elemental analysis for $C_{16}H_{18}O_2N_2S$: | | | |
|---|---|---|---|
| C | H | N | S |
| Calculated (%): 63.55 | 6.00 | 9.26 | 10.60 |
| Found (%): 63.45 | 6.05 | 9.20 | 10.71 |

Step (2) After reducing 24.0 g of the 3-diethylamino-4'-nitro-diphenyl sulfide obtained in Step (1) above in an autoclave in a hydrogen stream under a pressure of 50 kg/cm$^2$ in the presence of 4.0 g of Raney nickel catalyst and 100 ml of methyl alcohol for 3 hours at 40°–50° C., the Raney nickel catalyst was removed and the solvent was distilled away. Then, by removing benzene insoluble materials from the reaction mixture thus obtained, 21.2 g (yield 98%) of 3-diethylamino-4'-aminodiphenyl sulfide was obtained.

Boiling point: 180°–182° C./0.07 mmHg

| Elemental analysis for $C_{16}H_{20}N_2S$: | | | |
|---|---|---|---|
| C | H | N | S |
| Calculated (%): 70.54 | 7.40 | 10.28 | 11.77 |
| Found (%): 70.50 | 7.34 | 10.35 | 11.84 |

Step (3a) A mixture of 50 g of 3-diethylamino-4'-amino-diphenyl sulfide obtained in Step (2), 1.8 g of sodium acetate, 7.0 g of Raney nickel catalyst, 41 g of 90% acetaldehyde, and 1000 ml of methanol was placed in an autoclave and after charging hydrogen therein at 25 kg/cm$^2$, the reaction was performed for 4 hours at 50° C. Then, the reaction product was treated as in Step (2) and then recrystallized from isopropyl alcohol to provide 50.7 g (yield 84%) of 3,4'-bis-diethylaminodiphenyl sulfide.

Melting point: 46.0°–46.5° C.

| Elemental analysis for $C_{20}H_{28}N_2S$: | | | |
|---|---|---|---|
| C | H | N | S |
| Calculated (%): 73.12 | 8.59 | 8.52 | 9.76 |
| Found (%): 73.17 | 8.56 | 8.62 | 9.65 |

Step (3b) A mixture of 30 g of the 3-diethylamino-4'-amino-diphenyl sulfide obtained in Step (2), 200 g of benzyl chloride and 46 g of sodium carbonate was refluxed under heating for 20 hours in 200 ml of toluene. After the reaction was over, solid materials were filtered away and the filtrate was distilled under reduced pressure. The residue formed was mixed with 200 ml of methanol followed by stirring and the crystals formed were recovered by filtration to provide 47.4 g (yield 95%) of 3-diethylamino-4'-dibenzylamino-diphenyl sulfide having a melting point of 101°–106° C. The product was further recrystallized from ethyl acetate to provide 43.4 g (yield 87%) of the pure desired product having a melting point of 109°–110° C.

| Elemental analysis for $C_{30}H_{32}N_2S$: | | | |
|---|---|---|---|
| C | H | N | S |
| Calculated (%): 79.60 | 7.13 | 6.19 | 7.08 |
| Found (%): 79.60 | 7.05 | 6.16 | 7.18 |

Step (3c) A mixture of 25 g of the 3-diethylamino-4'-amino-diphenyl sulfide obtained in Step (2), 4.8 g of 90% acetaldehyde, 0.9 g of sodium acetate, 12 g of Raney nickel catalyst, and 100 ml of methanol was reacted in a 200 ml autoclave for 4 hours at 18°–22° C. while introducing therein hydrogen at 25 kg/cm$^2$. The reaction mixture obtained was recrystallized from ligroin as in Step (2) to provide 22.1 g (yield 80%) of 3-diethylamino-4'-ethylaminodiphenyl sulfide having a melting point of 41.0°–42.0° C.

| Elemental analysis for $C_{18}H_{24}N_2S$: | | | |
|---|---|---|---|
| C | H | N | S |
| Calculated (%): 71.95 | 8.05 | 9.32 | 10.67 |
| Found (%): 71.80 | 8.09 | 9.39 | 10.73 |

Step (3d) In 15 ml of acetic acid was dissolved 10 g of the 3-diethylamino-4'-ethylamino-diphenyl sulfide obtained in Step (3c) and after adding dropwise to the solution 3.9 g of acetic anhydride at 60° C., the mixture was reacted for 2 hours and a half, at 80° C. The reaction mixture obtained was poured into water followed by neutralization with sodium carbonate and then extracted with benzene. Then, by distilling away the solvent from the extract, 10.4 g (91%) of 3-diethylamino-4'-N-acetyl-N-ethylamino-diphenyl sulfide having a melting point of 181°–183° C./0.11 mmHg was obtained.

| Elemental analysis for $C_{20}H_{26}N_2OS$: | | | |
|---|---|---|---|
| C | H | N | S |
| Calculated (%): 70.14 | 7.65 | 8.18 | 9.36 |
| Found (%): 70.10 | 7.63 | 8.30 | 9.41 |

Step (3e) In 50 g of acetic acid was dissolved 25 g of the 3-diethylamino-4'-amino-diphenyl sulfide obtained in Step (2) and after adding dropwise to the solution 20 g of acetic anhydride at 60°–70° C., the mixture was reacted for 4 hours at 100° C. Then, by recrystallizing the reaction mixture from methanol as in Step (3d), 26.8 g (93%) of 3-diethylamino-4'-acetylamino-diphenyl sulfide was obtained.

Melting point: 112.0°–113.5° C.

| Elemental analysis for $C_{18}H_{22}N_2OS$: | | | |
|---|---|---|---|
| C | H | N | S |
| Calculated (%): 68.75 | 7.05 | 8.91 | 10.20 |
| Found (%): 68.85 | 7.09 | 9.02 | 10.22 |

Step (4) A mixture of 15.0 g of S-3-dimethylaminophenyl dimethylthiocarbamate (see, for example, M.S. Newman et al.; *J. Org. Chem.*, 31, 3980 (1966)) and 10.0 g of phthalic anhydride was reacted for 90 minutes at 130° C. in the presence of 4.5 g of aluminum chloride. The reaction mixture formed was decomposed and extracted with 5 N hydrochloric acid, rendered weakly alkaline with sodium carbonate, and the precipitate formed were removed by filtration. The filtrate formed was acidified with hydrochloric acid and the precipitate formed was recovered to provide 10.0 g of 2(4'-dimethylamino-2'-dimethylaminocarbonylthiobenzoyl)benzoic acid mono-hydrate. The melting point of the product could not be measured due to the presence of water.

| Elemental analysis for $C_{19}H_{20}N_2O_4S \cdot H_2O$: | | | |
|---|---|---|---|
| | C | H | N | S |
| Calculated (%): | 58.45 | 5.68 | 7.17 | 8.12 |
| Found (%): | 58.53 | 5.80 | 7.10 | 8.25 |

Step (5a) A mixture of 6 g of the 3,4-bis-diethylaminodiphenyl sulfied obtained in Step (3a) and 12 g of phthalic anhydride was reacted for one hour at 140° C. in the presence of 10 g of aluminum chloride. After cooling the reaction mixture to 50° C., 90 ml of concentrated sulfuric acid (98%) was added thereto gradually and the mixture was stirred for one hour at 130° C. The reaction product was then poured into ice water and rendered alkaline with sodium hydroxide. The product isolated was extracted with benzene and the extract was dried by concentration. Then, methanol was added to the residue and the precipitate formed was recovered and recrystallized from a mixture of benzene and methanol (about 2:1 by vol) to provide colorless crystals of 4.4 g (53%) of 3,7-bis-diethylamino-thiofluoran having a melting point of 187.5°–189.0° C.

| Elemental analysis for $C_{28}H_{30}N_2O_2S$: | | | |
|---|---|---|---|
| | C | H | N | S |
| Calculated (%): | 73.36 | 6.55 | 6.11 | 6.99 |
| Found (%) | 73.36 | 6.60 | 5.90 | 7.10 |
| $\lambda_{max}$* in 95% acetic acid solution: | 488 nm, 459 nm 684 nm, 405 nm | | | |

*The values of $\lambda_{max}$ correspond, in this order, to the maximum absorption, the second maximum absorption, the third maximum absorption and so on, respectively. The values of "$\lambda_{max}$" hereinafter given have the same meaning.

In the infrared absorption spectra, the characteristic absorption of the carbonyl of the lactone ring was marked at near 1750 cm$^{-1}$ in any aminothiofluoran compounds represented by general formula (I).

Step (5b) By conducting the same condensation reaction and the post treatment as in Step (5a) except using each of the 3-diethylamino-4'-acetylamino-diphenyl sulfide and the 3-diethylamino-4'-dibenzylamino-diphenyl sulfide obtained in Step (3e) and Step (3b), respectively, colorless crystals of 3-diethylamino-7-amino-thiofluoran having a melting point of 203.5°–205.0° C. were obtained.

| Elemental analysis for $C_{24}H_{22}O_2N_2S$: | | | |
|---|---|---|---|
| | C | H | N | S |
| Calculated (%): | 71.62 | 5.51 | 6.96 | 7.97 |
| Found (%): | 71.66 | 5.52 | 6.89 | 8.01 |
| $\lambda_{max}$ in 95% acetic acid solution: | 623 nm, 440 nm, 463 nm | | | |

Step (5c) By conducting the same condensation reaction and the post treatment as in Step (5a) except using each of the 3-diethylamino-4'-ethylamino-diphenyl sulfide and the 3-diethylamino-4'-N-acetyl-N-ethylamino-diphenyl sulfide obtained in Step (3c) and Step (3d), respectively, colorless crystals of 3-diethylamino-7-ethylamino-thiofluoran having a melting point of 111–112° C. was obtained.

| Elemental analysis for $C_{26}H_{26}N_2O_2S$: | | | |
|---|---|---|---|
| | C | H | N | S |
| Calculated (%) | 72.56 | 6.05 | 6.51 | 7.44 |
| Found (%): | 72.49 | 6.11 | 6.66 | 7.60 |

| Elemental analysis for $C_{26}H_{26}N_2O_2S$: | |
|---|---|
| $\lambda_{max}$ in 95% acetic acid solution: | 655, 450, 470 and 402 nm |

Step (5d) A mixture of 5 g of the 3-diethylamino-4'-dibenzylamino-diphenyl sulfide obtained in Step (3b) and 10 g of phthalic anhydride was melted at 140° C. in the presence of 8 g of aluminum chloride, the mixture was stirred for one hour and 30 minutes. The reaction mixture obtained was cooled to room temperature and after adding thereto 70 ml of concentrated sulfuric acid at a temperature below 25° C. to dissolve the product, the resultant mixture was stirred for 24 hours at room temperature. Then, by treating the reaction product as in Step (5a), 3.1 g (48%) of colorless crystals of 3-diethylamino-7-dibenzylamino-thiofluoran having a melting point of 138°–140° C. was obtained.

| Elemental analysis for $C_{38}H_{34}N_2O_2S$: | | | |
|---|---|---|---|
| | C | H | N | S |
| Calculated (%): | 78.35 | 5.84 | 4.81 | 5.50 |
| Found (%): | 78.30 | 5.88 | 4.81 | 5.40 |
| $\lambda_{max}$ in 95% acetic acid solution: | 662, 480, 452, and 402 nm | | | |

Step (5e) A mixture of 5 g of the 3-diethylamino-7-amino-thiofluoran obtained in Step (5b), 30 g of benzyl chloride, and 6 g of potassium carbonate was refluxed under heating. Solid materials formed were filtered off and the filtrate was distilled under reduced pressure. Then, methanol was added to the residue and the precipitate formed was recovered by filtration under suction and recrystallized from a mixture of benzene and methanol (about 2:1 by vol) to provide 5.6 g (77%) of 3-diethylamino-7-dibenzylaminothiofluoran as in Step (5d).

Step (5f) By conducting the same condensation reaction and the post treatment as in Step (5a) except using 6.0 g of 2,3'-bis-diethylamino-diphenyl sulfide as shown in Table 1 below, 4.0 g (48% yield) of 3,5-bis-diethylaminothiofluoran having a melting point of 176.5°–178.0° C. was obtained.

| Elemental analysis for $C_{28}H_{30}N_2O_2S$: | | | |
|---|---|---|---|
| | C | H | N | S |
| Calculated (%): | 73.36 | 6.55 | 6.11 | 6.99 |
| Found (%): | 73.20 | 6.57 | 6.15 | 6.90 |
| $\lambda_{max}$ in 95% acetic acid solution: | 581, 542, 500, 428, and 405 nm | | | |

Step (5g) By following the condensation reaction and the post treatment as in Step (5a) except that the 3,4'-bis-diethylamino-3'-methyl-diphenyl sulfide as shown in Table 1 below was used, 3,7-bis-diethylamino-6-methyl-thiofluoran having a melting point of 151.0°–152.5° C. was obtained.

| Elemental analysis for $C_{27}H_{28}N_2O_2S$: | | | |
|---|---|---|---|
| | C | H | N | S |
| Calculated (%): | 73.04 | 6.96 | 6.09 | 6.96 |
| Found (%): | 73.25 | 6.85 | 6.07 | 7.04 |
| $\lambda_{max}$ in 95% acetic acid solution: 576 and 535 nm | | | | |

Step (5h) By conducting the same condensation reaction and the post treatment as in Step (5a) except that the 3-diethylamino-4'-dimethylaminodiphenyl sulfide as shown in Table 1 below obtained from 3-nitro-4'-dimethylaminodiphenyl sulfide was used, 3-diethylamino-7-dimethylaminothiofluoran having a melting of 176.5°–178.1° C. was obtained.

| Elemental analysis for $C_{26}H_{26}N_2O_2S$: | | | | |
|---|---|---|---|---|
| | C | H | N | S |
| Calculated (%): | 72.53 | 6.09 | 6.51 | 7.45 |
| Found (%): | 72.43 | 6.11 | 6.60 | 7.50 |
| $\lambda_{max}$ in 95% acetic acid solution: | 457, 483, 666 and 405 nm | | | |

Step (5i) A mixture of 10.8 g of 2(4'-dimethylamino-2'-dimethylaminocarbonylthiobenzoyl)benzoic acid mono-hydrate obtained in Step (4) and 6.0 g of 4-hydroxydiphenylamine was reacted in 50 ml of concentrated sulfuric acid (98%) for 6 hours at 50° C. Then, by treating the reaction mixture obtained as in Step (5a), 5.0 g of 3-dimethylamino-7-anilinothiofluoran having a melting point of 256.0°–258° C. was obtained.

| Elemental analysis for $C_{28}H_{22}N_2O_2S$: | | | | |
|---|---|---|---|---|
| | C | H | N | S |
| Calculated (%): | 74.65 | 4.92 | 6.22 | 7.12 |
| Found (%): | 74.52 | 4.85 | 6.28 | 7.21 |
| $\lambda_{max}$ in 95% acetic acid solution: | 442, 466, and 600 nm | | | |

Step (5j) By following the same procedure as in Step (5i) except that 6.0 g of 2(4'-diethylamino-2'-dimethylaminocarbonylthiobenzoyl)benzoic acid obtained as in Step (4) and 2.5 g of 3-methyl-4-dimethylaminophenol were reacted for 2 hours at 90° C. using 25 ml of concentrated sulfuric acid (98%), 3-diethylamino-6-methyl-7-dimethylamino-thiofluoran was obtained. Melting point: 151.6°–152.9° C.

| Elemental analysis for $C_{27}H_{28}N_2O_2S$: | | | | |
|---|---|---|---|---|
| | C | H | N | S |
| Calculated (%): | 72.95 | 6.35 | 6.30 | 7.21 |
| Found (%): | 73.02 | 6.39 | 6.25 | 7.30 |
| $\lambda_{max}$ in 95% acetic acid solution: | 597, 435, and 410 nm | | | |

Step (5k) By following the same procedure as in Step (5j) except that p-aminoanisole was used and that the reaction was performed at 70° C. for 3 hours, 3-diethylamino-7-aminothiofluoran (5b) was obtained.

The properties of typical compounds represented by general formula (II) prepared according to the Production Examples as illustrated above are shown in Table 1.

By reacting the compounds shown in Table 1 and phthalic anhydride or the nucleus substituted derivatives thereof, the corresponding compounds of this invention represented by general formula (I) were obtained.

Table 1

| R' | $R_1'$ | $R_2$ | $R_3'$ | Physical Property |
|---|---|---|---|---|
| $(CH_3)_2N$ | H | H | $NO_2$ | mp. 91.0–92.5° C |
| $(CH_3)_2N$ | H | H | $NH_2$ | mp. 78.0–79.0° C |
| $(CH_3)_2N$ | H | H | $N(CH_3)_2$ | mp. 89.5–91.0° C |
| $(C_2H_5)_2N$ | H | H | $N(CH_3)_2$ | mp. 75.4–76.8° C |
| $(C_2H_5)_2N$ | $NO_2$ | H | H | bp. 178–180° C/0.10 mmHg |
| $(C_2H_5)_2N$ | $(C_2H_5)_2N$ | H | H | bp. 158–162° C/0.06 mmHg |
| $(C_2H_5)_2N$ | H | $CH_3$ | $NH_2$ | bp. 180–185° C/0.06 mmHg |
| $(C_2H_5)_2N$ | H | $CH_3$ | $N(CH_3)_2$ | mp. 181.0–182.0° C (hydrochloride) |
| $(C_2H_5)_2N$ | H | $CH_3$ | $N(C_2H_5)_2$ | bp. 157–159° C/0.08 mmHg |
| $(C_2H_5)_2N$ | H | $CH_3$ | $NO_2$ | mp. 175.0–179.0° C (hydrochloride) |
| $(C_2H_5)_2N$ | $NO_2$ | H | $NO_2$ | mp. 121.5–123.0° C |
| $(C_2H_5)_2N$ | H | H | (NH-phenyl with NO₂, NO₂ substituents) | mp. 137.0–139.0° C |
| $(C_2H_5)_2N$ | H | H | (NH-CH₂-phenyl) | mp. 70.5–71.5° C |
| $(C_2H_5)_2N$ | H | H | (N(SO₂-phenyl)(CH₂-phenyl)) | mp. 110.5–113.5° C |

Table 1-continued

[Structure: R'-phenyl-S-phenyl with R₁', R₂, R₃' substituents]

| R' | R₁' | R₂ | R₃' | Physical Property |
|---|---|---|---|---|
| $(C_2H_5)_2N$ | H | H | | mp. 194.0–197.0° C |
| $(C_2H_5)_2N$ | H | H | [SO₂-phenyl / N-Na / NH / N-cyclohexyl group] | mp. 33.5–35.5° C<br>bp.173–175° C/0.08 mmHg |
| $NO_2$ | H | $CH_3$ | $N(CH_3)_2$ | mp. 188.0–189.9° C (perchlorate) |
| $NH_2$ | H | $CH_3$ | $N(CH_3)_2$ | mp. 120.0–122.0° C (hydrochloride) |

[Structure: O₂N-phenyl-S-carbazole type, N-CH₃] — mp. 134.0–138.0° C

[Structure: H₂N-phenyl-S-carbazole type, N-CH₃] — mp. 132.0–133.0° C

[Structure: (C₂H₅)₂N-phenyl-S-carbazole type, N-CH₃] — mp. 121.0–123.0° C

Step (6a) In 100 ml of ethanol were dissolved 8 g of 3,6-bis-diethylamino-thiofluoran perchlorate represented by formula (V) prepared by process (C) or process (D) described hereinbefore and 8 g of ammonia, and the solution thus obtained was charged in a 200 ml autoclave to perform the reaction for 2 hours at 150° C. After cooling the reaction mixture, and crystals thus precipitated were recovered by filtration and recrystallized from a mixture of benzene and metanol (about 3:1 by vol) to provide 4.5 g of colorless lactam of 2-[3,6-bis-diethylamino-9-amino-thioxanthyl]-benzoic acid having a melting point of 247.5°–249.0° C.

Elemental analysis for $C_{26}H_{31}N_3OS$:

| | C | H | N | S |
|---|---|---|---|---|
| Calculated (%): | 72.06 | 7.16 | 9.70 | 7.39 |
| Found (%): | 72.00 | 7.25 | 9.67 | 7.34 |

$\lambda_{max}$ in 95% acetic acid solution: 576 and 535 nm.

Step (6b) A mixture of 5 g of the 3,6-bis-diethylaminothiofluoran represented by general formula (V) and 8 g of cyclohexylamine was refluxed under heating for 7 hours. The reaction mixture was poured into 700 ml of ice and the precipitate formed was recovered by filtration under suction, washed with methanol, and recrystallized from benzene to provide 2.1 g of lactam of 2-[3,6-bis-diethylamino-9-cyclohexylamino-thioxanthyl]-benzoic acid having a melting point of 135.0°–137.0° C.

Elemental analysis for $C_{32}H_{40}N_3OS$:

| | C | H | N | S |
|---|---|---|---|---|
| Calculated (%): | 75.70 | 7.61 | 7.79 | 5.94 |
| Found (%): | 75.79 | 7.48 | 7.76 | 5.95 |

$\lambda_{max}$ in 95% acetic acid solution: 577 and 535 nm.

Step (6c) By following the same procedure as in Step (6b) except that phenylhydrazine was used, colorless lactam of anhydro[2-(3,6-bis-diethylamino-9-phenylhydrazinothioxanthyl)-benzoic acid] having a melting point of 186.0°–187.5° C. was obtained.

Elemental analysis for $C_{32}H_{36}N_4OS$:

| | C | H | N | S |
|---|---|---|---|---|
| Calculated (%): | 74.45 | 6.57 | 10.22 | 5.84 |
| Found (%): | 74.40 | 6.56 | 10.14 | 5.98 |

$\lambda_{max}$ in 95% acetic acid solution: 579 and 535 nm.

Step (6d) In 10 g of aniline was added 5 g of 3,6-bis-diethylaminothiofluoran and heated to dissolve at 70° C. After adding dropwise thereto 5 g of phosphrous oxychloride, the resultant solution was refluxed for 3 hours, and a steam distillation was conducted to obtain a precipitate. The thus obtained precipitate was extracted with toluene and recrystallized to provide substantially colorless crystals of 3.5 g of lactam of 2-[3,6-bis-diethylamino-9-anilinothioxanthyl]-benzoic acid having a melting point of 274°–277.0° C.

Elemental analysis for $C_{34}H_{35}N_3OS$:

|  | C | H | N | S |
|---|---|---|---|---|
| Calculated (%): | 76.51 | 6.61 | 7.87 | 6.01 |
| Found (%): | 76.40 | 6.59 | 7.81 | 6.15 |

$\lambda_{max}$ in 95% acetic acid solution: 577 and 535 nm.

Production examples of the 3,6-bis-substituted aminofluoran derivatives represented by general formula (V), which were used in the above examples, by process (C) and process (D) are illustrated below.

Process (C) A mixture of 10 g of N,N-diethylamino-m-thiophenol (boiling point 103°–105° C./0.2 mmHg) prepared according to the process described in M. S. Newman and H. A. Karnes; *J. Org. Chem.*, 31, 3980 (1966) and 4.1 g of phthalic anhydride was reacted for 1.5 hours at 140° C. in the presence of 8.2 g of aluminum chloride. After cooling the reaction mixture to room temperature, 700 ml of ice water was added to the reaction mixture. The mixture was neutralized with sodium carbonate and the product was extracted with chloroform. The solvent was distilled away from the extract and the residue was recrystallized from a mixture of methanol and benzene to provide 3,6-bis-diethylamino-thiofluoran having a melting point of 134°–136° C.

Also, 12.5 g (yield 81%) of the perchlorate thereof was obtained as red-green crystals. The perchlorate decomposed at 250° C.

Elemental anlysis for $C_{28}H_{31}ClN_2O_6S$:

|  | C | H | N | S |
|---|---|---|---|---|
| Calculated (%): | 60.16 | 5.55 | 5.01 | 5.73 |
| Found (%): | 60.22 | 5.53 | 4.83 | 5.62 |

$\lambda_{max}$ in 95% acetic acid solution: 576 and 535 nm.

Process (D) In 40 ml of acetic anhydride were dissolved 10 g of N,N-diethylamino-m-thiophenol and 17.3 g of o-(4-diethylamino-2-hydroxybenzoyl)benzoic acid at 60° C. and after adding thereto 8.3 g of zinc chloride, the mixture was refluxed under heating for one hour. The reaction mixture was added to ice water and treated as in the above-described Process (C) to provide 24.0 g (78% yield) of the perchlorate of 3,6-bis-diethylamino-thiofluoran.

The pressure-sensitive copying elements of this invention may be prepared using the aminothiofluoran compounds or the aminothiofluoran-γ-lactam compounds represented by general formula (I) as chromogenic materials using, for example, the process of preparing oil-containing microcapsules as described in the specifications of U.S. Pat. Nos. 2,548,366 and 2,800,457. Also, in the case of producing heat-sensitive recording papers using these compounds of this invention, the processes as described in, for example, Japanese patent publication Nos. 6040/'65; 4160/'68 and 14,039/'70 can be utilized. In these cases, the compounds of this invention represented by general formula (I) can be used individually or as a combination of two or more thereof, or further, as the case may be, in combination with known chromogenic materials.

Examples of the production of pressure-sensitive copying elements and heat-sensitive recording element using typical examples of the compounds of this invention represented by the general formula (I) as chromogenic materials are illustrated below in detail.

EXAMPLE 1

In 100 g of diisopropylnaphthalene (KMC-113, a trade name, made by Kureha Kagaku K. K.) was dissolved 3.0 g of 3-diethylamino-7-amino-thiofluoran (produced as described in the Production Examples, Step (5b) above) and the solution was emulsified by adding thereto 20 g of gum arabic and 160 g of water at 50° C. To the emulsion were added 20 g of acid-treated gelatin and 160 g of water and the pH of the mixture was adjusted to 5 by adding thereto acetic acid with stirring. Then, 500 g of water was added to the mixture to cause coacervation, whereby concentrated liquid films of gelatin-gum-arabic were found around the oil droplets of diisopropylnaphthalene containing the chromogenic material therein. Thereafter, acetic acid was further added dropwise to the system to adjust the pH thereof to 4.4 and then 3.8 g of a 37% aqueous formaldehyde solution was added to harden the above-mentioned liquid films. Thereafter, the system was cooled to 10° C., and after adjusting the pH thereof to 9 by adding an aqueous solution of sodium hydroxide, the system was allowed to stand for 5–6 hours to complete the formation of the capsules.

The microcapsule-containing dispersion was coated on a paper by roll coating or air knife coating in an amount of about $5g/m^2$ of the dispersion and dried.

The coated paper (base sheet) thus prepared was closely superposed on a paper (undersheet) prepared by coating on a paper an acid electron accepting adsorber such as, for example, acid clay and/or a phenol-formaldehyde resin and when a localized pressure was applied onto the assembly using a ball pen or typewriting, clear dark green marks were formed quickly on the surface of the undersheet. The dark green dye formed from the chromogenic material exhibited sufficient light resistance and water resistance for practical use as well as exhibited excellent stability in long storage.

EXAMPLE 2

A base paper was prepared by following the same procedures as in Example 1 using 2.0 g of 3-diethylamino-7-dibenzylamino-thiofluoran (produced as described in the Production Examples, Step (5d), above) as the chromogenic material and when the base paper was closely superposed on an undersheet and locally pressed as in Example 1, clear green marks were formed quickly on the surface of the undersheet. The green dye formed exhibited very excellent stability in long storage.

EXAMPLE 3

A base paper was prepared by following the same procedure as in Example 1 using 2.5 g of 3,5-bis-diethylaminothiofluoran (produced as described in the Production Examples, Step (5d), above) as the chromogenic material and when the base paper was closely superposed on an undersheet and locally pressed as in Example 1, clear red-purple marks were formed quickly. The dye formed showed excellent stability on long storage.

EXAMPLE 4

The same procedure as in Example 1 was followed except that 1.0 g of 3-diethylamino-7-ethylaminothiofluoran (produced as described in the Production Examples, Step (5c), above), 1.2 g of 3,6-dimethoxyfluoran, 0.6 g of Crystal Violet lactone, and 0.5 g of 3-diethylamino-6-methyl-7-chlorofluoran were used as the chromogenic materials. When the pressure-sensitive copying paper or the assembly of the base paper and an undersheet were locally pressed as in Example 1, clear black marks were formed quickly. The dyes formed exhibited excellent stability in long storage.

EXAMPLE 5

After adding 15g of a 10% aqueous solution of polyvinyl alcohol and 20 ml of water to 1 g of 3,7-bis-diethylamino-6-methylthiofluoran (produced as described in the Production Examples, Step (5g), above), the mixture was treated in a ball mill for 24 hours to pulverize and disperse the thiofluoran. Furthermore, 2 g of bisphenol A was mixed with 12 g of 10 % polyvinyl alcohol and 15 ml of water and the mixture was treated in a ball mill for 24 hours to pulverize and disperse the bisphenol A.

Both dispersions prepared were mixed with each other and the mixture was coated on a paper and dried to provide a heat-sensitive recording paper. Dark purple-green marks were quickly formed on the sensitive recording paper using a heated pen or heated type.

EXAMPLE 6

By following the same procedure as in Example 1 except that the chromogenic material prepared in the Production Examples, Step (6b) was used, a base paper was prepared and when the base paper was superposed on an undersheet and locally pressed as in Example 1, clear dark red-purple marks were formed on the undersheet. The dye formed from the chromogenic material exhibited sufficient light resistance and water resistance for practical use and further exhibited excellent stability in long storage.

EXAMPLE 7

By following the same procedure as in Example 1 except that 1.0 g of the chromogenic material prepared in the Production Examples, Step (6c) above, 0.8 g of Crystal Violet lactone, 0.5 g of benzoyl leucomethylene blue, and 1.2 g of 3,6-diethoxyfluoran were used as the chromogenic materials, a base paper was prepared and when the base paper was superposed on an undersheet and locally pressed as in Example 1, clear black marks were formed. The dyes formed exhibited excellent stability in long storage.

Moreover, heat-sensitive recording papers were also prepared using the aminothiofluoran-γ-lactam compounds of this invention, for example, the lactam compounds prepared in the Productions Examples, Steps (6a), (6b), (6c) and (6d), above. These heat-sensitive recording papers exhibited very satisfactory coloring results either using infrared iradiation or the application of heated type.

While the invention has been described in detail and with reference to specific embodiments thereof, it will be apparent to one skilled in the art that various changes and modifications can be made therein without departing from the spirit and scope thereof.

What is claimed is:

1. A compound represented by the general formula (I)

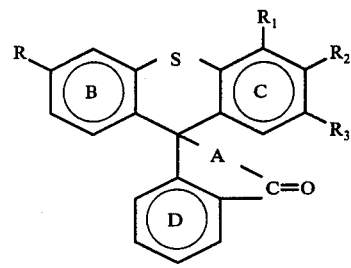

wherein A represents an oxygen atom or a group selected

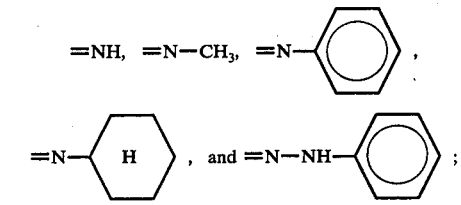

and when A is an oxygen atom, R represents amino, methylamino, ethylamino, dimethylamino, diethylamino, N-acetyl-N-ethyl-amino, naphthalenemethyl amino, N-ethyl-N-benzylamino, N-benzylamino, anilino, N-ethylanilino, N-acetylanilino, N,N-diphenylamino, N-methyltoluidino, carboxyanilino, carboxynaphthylamino, phenylanilino, N-benzylanilino, pyrrolidino, piperidino, morpholino, cyclohexylamino, N-ethyl-N-cyclohexylamino, dibenzylamino, phenylacetamido, toluoylamino, acetamido, N-benzyl-N-phenylsulfonamido, toluene sulfonamido or phenylsulfonamido; $R_1$ and $R_3$, which may be the same or different, each represents a hydrogen atom, a lower alkyl group, a nitro group, amino, methylamino, ethylamino, dimethylamino, diethylamino, N-acetyl-N-ethyl-amino, naphthalenemethyl amino, N-ethyl-N-benzylamino, N-benzylamino, anilino, N-ethylanilino, N-acetylanilino, N,N-diphenylamino, N-methyltoluidino, carboxyanilino, carboxynaphthylamino, phenylanilino, N-benzylanilino, pyrrolidino, piperidino, morpholino, cyclohexylamino, N-ethyl-N-cyclohexylamino, dibenzylamino, phenylacetamido, toluoylamino, acetamido, N-benzyl-N-phenylsulfonamido, toluene sulfonamido or phenylsulfonamido; and $R_2$ represents a hydrogen atom or a lower alkyl group; wherein $R_1$ and $R_2$ or $R_2$ and $R_3$ may combine with benzene ring C to form a naphthalene nucleus, indole or carbazole; and when A is not an oxygen atom, R represents

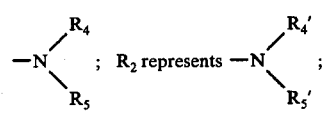

$R_4$, $R_5$, $R_4'$ and $R_5'$, which may be the same or different, each represents a hydrogen atom or a lower alkyl group; and $R_1$ and $R_3$ each represents a hydrogen atom.

2. An aminothiofluoran compound represented by the general formula (Ia)

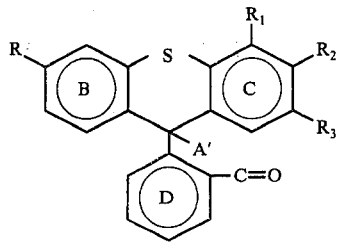

wherein A′ represents an oxygen atom; R represents amino, methylamino, ethylamino, dimethylamino, diethylamino, N-acetyl-N-ethylamino, naphthalenemethyl amino, N-ethyl-N-benzylamino, N-benzylamino, anilino, N-ethylanilino, N-acetyl-anilino, N,N-diphenylamino, N-methyltoluidino, carboxyanilino, carboxynaphthylamino, phenylanilino, N-benzylanilino, pyrrolidino, piperidino, morpholino, cyclohexylamino, N-ethyl-N-cyclohexylamino, dibenzylamino, phenylacetamido, toluoylamino, acetamido, N-benzyl-N-phenylsulfonamido, toluenesulfonamido or phenylsulfonamido; $R_1$ and $R_3$, which may be the same or different, each represents a hydrogen atom, a lower alkyl group, a nitro group, amino, methylamino, ethylamino, dimethylamino, diethylamino, N-acetyl-N-ethylamino, naphthalenemethyl amino, N-ethyl-N-benzylamino, N-benzylamino, anilino, N-ethylanilino, N-acetylanilino, N,N-diphenylamino, N-methyltoluidino, carboxyanilino, carboxynaphthylamino, phenylanilino, N-benzylanilino, pyrrolidino, piperidino, morpholino, cyclohexylamino, N-ethyl-N-cyclohexylamino, dibenzylamino, phenylacetamido, toluoylamino, acetamido, N-benzyl-N-phenylsulfonamido, toluene sulfonamido or phenylsulfonamido; $R_2$ represents a hydrogen atom or a lower alkyl group; $R_1$ and $R_2$ or $R_2$ and $R_3$ may combine with benzene ring C to form a naphthalene nucleus, indole or carbazole.

3. An aminothiofluoran-γ-lactam compound represented by the general formula (Ib)

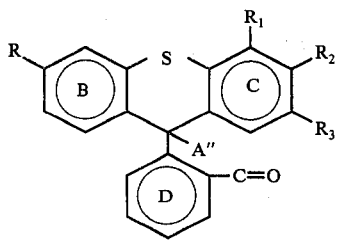

wherein A″ represents a group selected from =NH, =N—CH$_3$,

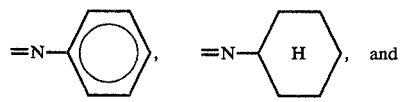 and

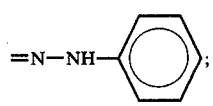;

R represents

$R_2$ represents

$R_4$, $R_4′$, $R_5$ and $R_5′$ which may be the same or different, each represents a hydrogen atom or a lower alkyl group: $R_1$ and $R_3$ each represent a hydrogen atom.

4. A process for producing an aminothiofluoran compound represented by the general formula (Ia)

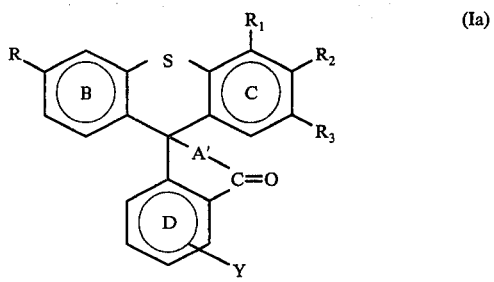

(Ia)

wherein R, $R_1$, $R_2$, $R_3$, and A′ have the same significance as defined in claim 2; and Y represents a hydrogen atom, a halogen atom, or a nitro group which comprises reacting a diphenyl sulfide derivative represented by general formula (II)

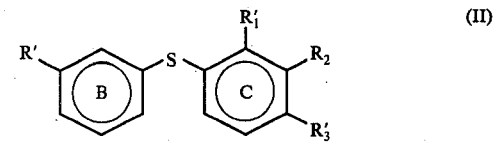

(II)

wherein R′ represents a substituted amino group; $R_1′$ and $R_3′$, which may be the same or different, each represents a hydrogen atom, a lower alkyl group, a nitro group, an amino group or a substituted amino group; and $R_2$ represents a hydrogen atom or a lower alkyl group; $R_1′$ and $R_2$ or $R_2$ and $R_3′$ may combine with benzene ring C to form a naphthalene nucleus of a nitrogen-containing heterocyclic ring; with phthalic anhydride or a nucleus substituted derivatives thereof.

5. A process for producing an aminothiofluoran compound represented by general formula (Ia)

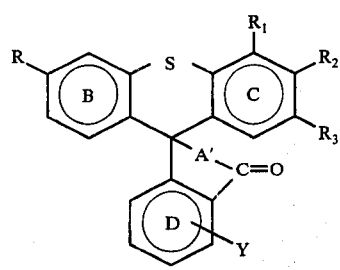

wherein R, $R_1$, $R_2$, $R_3$, and A′ have the same significance as defined in claim 2 and Y represents a hydrogen atom, a halogen atom or a nitro group; which comprises reacting a benzoylbenzoic acid derivative represented by general formual (III)

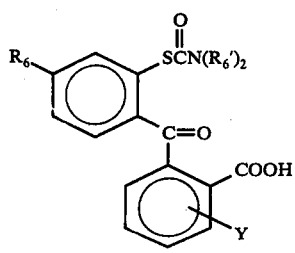 (III)

wherein $R_6$ represents a substituted amino group; $R_6'$ represents a lower alkyl group; and Y has the same significance as defined above or the hydrate thereof; with a phenol derivative represented by general formula (IV)

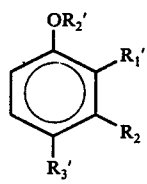

wherein $R_2$ and $R_2'$, which may be the same or different, each represents a hydrogen atom or a lower alkyl group; and $R_1'$ and $R_3'$, which may be the same or different, each represents a hydrogen atom, a lower alkyl group, a nitro group, an amino group or a substituted amino group; $R_1'$ and $R_2$ or $R_2$ and $R_3'$ may combine with the benzene ring to form a naphthalene nucleus or a nitrogen-containing heterocyclic ring.

6. A recording member comprising a support having therein or thereon a recording composition containing at least one compounds represented by the general formula (I).

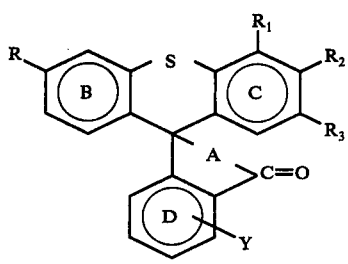 (I)

wherein R, $R_1$, $R_2$, $R_3$, and A each is as defined in claim 1 and Y represents a hydrogen atom, a halogen atom or a nitro group.

7. The coloring record member as claimed in claim 6, wherein said coloring record member is a pressure-sensitive copying element.

8. The coloring record member is claimed in claim 6, wherein said coloring record member is a heat-sensitive recording element.

9. A process of producing an aminothiofluoran compound represented by general formula (V)

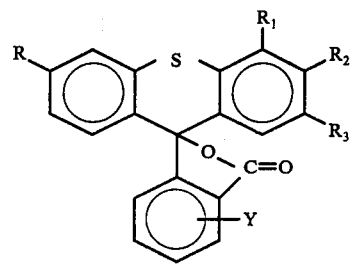

wherein R represents

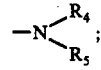

$R_2$ represents

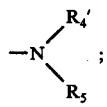

$R_4$, $R_4'$, $R_5$ and $R_5'$ which may be the same or different, each represents a hydrogen atom or a lower alkyl group; $R_1$ and $R_3$ each represents a hydrogen atom; and Y represents a hydrogen atom, a halogen atom or a nitro group or an acid addition salt of said aminothiofluoran compound represented by general formula (V); which comprises reacting a m-substituted aminothiophenol compound with phthalic anhydride or a nucleus substituted derivative thereof in the presence of a Friedel-Craft catalyst in the absence or the presence of a solvent selected from the group consisting of carbon disulfide, tetrachloroethane, nitrobenzene and chlorobenzene, and if necessary, converting said aminothiofluoran compound represented by general formula (V) to the acid addition salt thereof.

10. The process of claim 9, wherein the m-substituted aminothiophenol compound and the phthalic anhydride or a nucleus substituted derivative thereof are melted in the presence of the Friedel-Craft catalyst in the absence of a solvent.

11. The process of claim 10, wherein the Friedel-Craft catalyst is an aluminum chloride, a stannic chloride, a zinc chloride or a boron trifluoride, 12. A process of producing an aminothiofluoran compound represented by general formula (V)

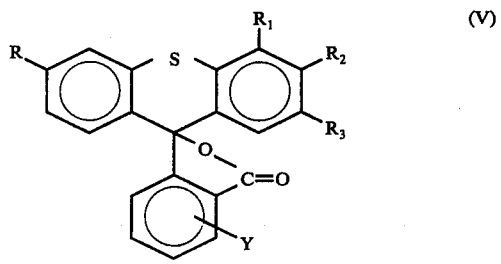 (V)

wherein R represents $R_2$ represents

$R_4$, $R_4'$, $R_5$ and $R_5'$, which may be the same or different, each represents a hydrogen atom or a lower alkyl group; $R_1$ and $R_3$ each represents a hydrogen atom; and Y represetns a hydrogen atom, a halogen atom or a nitro group or an acid addition salt of said aminothiofluoran compound represented by general formula (V); which comprises reacting a m-substituted aminothiophenol compound with a 2-(4'-substituted amino-2'hydroxybenzoyl)-4-(or -5-) substituted benzoic acid which may be unsubstituted or substituted in the 4- or 5-position of the benzene ring of said benzoic acid in the presence or absence of a Friedel-Craft catalyst using a condensing agent selected form the group consisting of polyphosphoric acid, phosphoric anhydride, acetic anhydride, acetic acid, phosphorus pentoxide and phosphorous oxychloride, and if necessary, converting said aminothiofluoran compound represented by general formula (V) to the acid addition salt thereof.

13. The process of claim 12, the reaction being performed in acetic anhydride as a solvent in the presence of the Friedel-Craft catalyst.

14. The process of claim 13, wherein the Friedel-Craft catalyst is an aluminum chloride, a stannic chloride, a zinc chloride or a boron trifluoride.

15. The compound of claim 1 wherein the D ring is substituted by a halogen atom or a nitro group.

16. The compound of claim 2 wherein the D ring is substituted by a halogen atom or a nitro group.

17. The compound of claim 3 wherein the D ring is substituted by a halogen atom or a nitro group.

18. The process of claim 4 wherein the nitrogen-containing heterocyclic ring is an indole or a carbazole.

19. The process of claim 5 wherein the nitrogen-containing heterocyclic ring is an indole or carbazole.

* * * * *